United States Patent [19]

Drouault

[11] Patent Number: 5,962,032

[45] Date of Patent: Oct. 5, 1999

[54] PHARMACEUTICAL COMPOSITIONS FOR CONTROLLING UNITARY SMOOTH MUSCLE POLARIZATION

[76] Inventor: Guy Drouault, 2 Chemin de la Butte-au-Diable, 91570 Bievres, France

[21] Appl. No.: 08/894,798

[22] PCT Filed: Mar. 12, 1996

[86] PCT No.: PCT/FR96/00382

§ 371 Date: Sep. 12, 1997

§ 102(e) Date: Sep. 12, 1997

[87] PCT Pub. No.: WO96/28172

PCT Pub. Date: Sep. 19, 1996

[30] Foreign Application Priority Data

Mar. 13, 1995 [FR] France .................................. 95 02880

[51] Int. Cl.$^6$ .................................................. A61K 33/30
[52] U.S. Cl. ................................ 424/679; 424/6; 424/78; 424/680; 424/681; 514/23; 514/561
[58] Field of Search .................................. 424/6, 78, 679, 424/680, 681; 514/23, 561

[56] References Cited

FOREIGN PATENT DOCUMENTS 2 602 678   2/1988   France .

OTHER PUBLICATIONS

Ca 122:38851, Arii et al, Oct. 4, 1994.

*Primary Examiner*—Rebecca Cook
*Attorney, Agent, or Firm*—Dennison, Meserole, Scheiner & Schultz

[57] ABSTRACT

Pharmaceutical compositions for regulating unitary smooth muscle polarization containing aqueous solutions based on magnesium, potassium, sodium and optionally calcium salts, at least one sugar and at least one amino acid, combined with a copper salt or a zinc salt. The invention further relates to a kit containing at least two of these pharmaceutical compositions.

14 Claims, No Drawings

PHARMACEUTICAL COMPOSITIONS FOR CONTROLLING UNITARY SMOOTH MUSCLE POLARIZATION

This is a 371 of PCT/FR96/00382 filed Mar. 12, 1996.

BACKGROUND OF THE INVENTION

The present invention relates to pharmaceutical compositions for regulating unitary smooth muscle polarization. The invention further relates to a kit containing at least two of the above pharmaceutical compositions.

Patent FR 2 602 678 has already described aqueous pharmaceutical compositions based on magnesium, sodium and potassium salts for regulating the local circulations, which are particularly suitable in the treatment of recurring disorders and diseases of the upper respiratory tract.

These compositions consist of an aqueous solution containing magnesium, potassium, sodium and optionally calcium salts in combination with at least one sugar and at least one amino acid.

The sugar contained in these compositions is an absorbable sugar selected from glucose, galactose and xylose, or optionally a non-absorbable sugar such as mannitol.

The amino acid contained in these compositions is selected from arginine, phenylalanine and glutamic acid.

Apart from its role in conveying the inspired air, the respiratory tract is responsible for translating and processing the airborne information arriving from the outside world. Its essential task is to free the inspired air of the inert or living particles it contains. The respiratory tract does this by deploying several barriers on its surface for neutralizing the airborne contaminants:

the mucociliary barrier the commensal micro-organism barrier the secretory IgA barrier.

However, whereas along the whole of the respiratory tract this trapping of the contaminants depends on random contact with the wall, at the rhinosinusal stage there is a dynamic structure which consists of a very dense vascular network with erectile tissue and whose variations in volume have a dual effect: to channel and precipitate the aerial contaminants onto the mobile mucociliary barrier, and to connect the sinusal surfaces to the respiratory system.

This apparatus is driven by unitary smooth muscle tissue. The unitary smooth muscles have the characteristic property of contracting spontaneously, excited only by local factors (physical factors, for example stretching, and chemical or metabolic factors). They drive the microcirculation and the mucociliary function of the respiratory mucosae. Whatever its nature, the information received modifies the membrane polarity of this muscle tissue and generates action potentials with which a contraction is associated. This automatic activity is initiated in stimulating cells (of the pacemaker type) variably located in the tissue, and propagates to all the tissue as though a single structure were involved.

This spontaneous activity, which is only modulated and not triggered by their innervation, permits local autoregulation. It is this tissue which constitutes the muscle cells of the capillary sphincters and of the arteriovenous anastomosis, the myofibrils of the secretory cells and glands and the contractile proteins of the ciliated cells. This is how this apparatus can be autoregulated by the air stream and the airborne contaminants which carry the physical information, and by local metabolic factors which carry the pharmacological information, the autonomous nervous system only coming into play for punctual actions of defense or adaptation of the mucosa.

The transduction of this information is not biochemical but biophysical: action potentials are spontaneously generated whatever the information: physical, chemical or metabolic. A contraction of the unitary smooth muscle tissue is associated with the volley of action potentials and drives the microcirculation and the mucociliary system, and this contraction is not only well synchronized but also modulated by the excitation and adapted to the excitation by virtue of the action potentials, which can vary in number, amplitude and frequency. This so-called phase contraction is the functional contraction.

It is excessive variations in the membrane polarity which will dysregulate this apparatus. Strong excitations or strong inhibitions carried by endogenous factors and (or) exogenous factors can cause the muscle membrane to break through a polarization or depolarization threshold beyond which the spontaneous generation of action potentials is abolished. A tonic contraction is then set up which is uniform and dysregulatory because it depends on passive calcium ion movements not modulated by the information.

Depending on the etiological factors, the abolition of the action potentials can in the first instance electively dysregulate the microcirculatory function or the mucociliary function and thereby create various pathogenic processes. Two are particularly important on account of their frequency and their major role in the initiation of disorders and diseases of the upper respiratory tract.

Dysregulation of the contraction of one or both capillary sphincters or the muscular tunic of the arteriovenous anastomosis causes a vasomotor disorder of variable clinical expression: in the first case, for example, this is initially a mechanical edema, but the ionic and metabolic perturbations which have been triggered generate a tissue edema.

Dysregulation of the contraction of the mucociliary contractile proteins causes hypersecretion or hyposecretion with ciliary dyskinesia. Dehydration of the mucosa, in particular, is a formidable disorder. In the absence of a mucociliary barrier, the contaminants will behave like airborne particles and, in contact with the mucosa, will either trigger an immune reaction, if they attach themselves thereto or penetrate it, or exhibit a pathogenic physical action. This action varies with the charge, mass, speed and angle of impact of the contaminants. Whether the action exhibited is mechanical, caloric or electromagnetic, it is a source of hemodynamic perturbations and non-specific inflammatory reactions, with vasomotor disorders.

SUMMARY OF THE INVENTION

The pharmaceutical compositions according to the invention make it possible to regulate the polarization of unitary smooth muscles deregulated by hyperpolarization or by hyperdepolarization; they thus cause the spontaneous regeneration of action potentials and the restoration of the phase contraction of said unitary smooth muscles, thereby disabling the mechanisms responsible for the initiation of the vasomotor disorder, the secretory disorder and, consequently, the non-specific inflammation.

The pharmaceutical compositions according to the invention are aqueous solutions containing magnesium, potassium, sodium and optionally calcium salts, at least one sugar and at least one essential amino acid in combination with a copper salt or a zinc salt.

DETAILED DESCRIPTION OF THE INVENTION

The magnesium, potassium, sodium and optionally calcium salts used in the composition according to the invention are pharmaceutically acceptable salts. They can be chlorides, sulfates, phosphates or lactates, for example.

The sugars are used in the dextrorotatory form.

Examples which may be mentioned of sugars appropriate for the purposes of the invention are any absorbable sugars, such as glucose, galactose and xylose, and their structural analogs having a hydroxyl in the α-position on carbon 2.

A non-absorbable sugar, such as mannitol, which promotes the development of an electrochemical gradient, can also be used in combination with an absorbable sugar. It is also a good scavenger of OH.free radicals.

The amino acids included in the composition of the invention are glucogenic compounds. The levorotatory form will preferably be used.

Examples which may be mentioned of amino acids appropriate for the purposes of the invention are L-phenylalanine, L-arginine and glutamic acid. It may be noted that L-phenylalanine is both glucogenic and ketogenic. The amount of amino acid can vary between 1 and 20 g per liter.

The amount of salts to be used in the composition according to the invention can vary within wide limits. However, it may be pointed out that the salt concentration can advantageously range from about 10 mg per liter to 2000 mg per liter and is preferably between 40 and 800 mg per liter. When potassium chloride is used, the potassium salt concentration is advantageously between 10 mg per liter and 300 mg per liter.

The total amount of sugar in the composition according to the invention can vary between 200 and 10,000 mg per liter. When a non-absorbable sugar is used, its concentration is of the order of 200 to 900 mg per liter.

As indicated previously, the magnesium, sodium and potassium salts are essential for the purposes of the invention, whereas the calcium salts are not.

It may be noted that, depending on the weight ratio K/Mg, the compositions obtained have a depolarizing effect or a polarizing effect on the unitary smooth muscles. Thus, if the ratio K/Mg is less than 1, preferably between 0.40 and 0.85, the composition according to the invention will have a depolarizing effect, whereas with a weight ratio K/Mg of between 14 and 16, the composition obtained will have a polarizing effect. In the latter case, chlorides are preferably used as the salts, the chosen weight ratio K/Na advantageously being between 30 and 40.

The copper and zinc salts appropriate for the purposes of the invention are selected from the water-soluble salts of these metals, for example the sulfate, the gluconate, the digluconate, the carbonate etc., copper gluconate and zinc chloride being particularly preferred.

The amounts of zinc metal and copper metal can vary between 5 and 120 mg/l in the case of zinc and between 5 and 100 mg/l in the case of copper.

The pharmaceutical compositions according to the invention are particularly indicated in the treatment of vasomotor disorders, secretory disorders and acute and especially subacute inflammatory disorders of the upper respiratory mucosae, since they regulate the polarization of the unitary smooth muscles driving the microcirculation and the mucociliary function of these mucosae, and re-establish the physiological biophysical mechanism for transducting the information within these tissues.

In particular, they make it possible to clear the nasal cavities, the sinuses and the eustachian tubes, even in cases of viral superinfection or bacterial super-infection.

The pharmaceutical compositions according to the invention are also indicated in the treatment of tracheobronchial diseases and intrinsic (or non-allergic) asthma. In fact, deregulation of the unitary smooth muscles is responsible for the vasomotor disorders, secretory disorders and non-specific inflammation which will modify the tracheobronchial lumen.

The pharmaceutical compositions according to the invention also make it possible to clear the tear ducts.

According to another feature, the invention further relates to a kit for regulating unitary smooth muscle polarization, this kit comprising at least two pharmaceutical compositions as defined above. The pharmaceutical compositions contained in this kit can be administered simultaneously, successively or separately, preferably successively. The kit according to the invention preferably comprises two pharmaceutical compositions according to the invention, one having a polarizing effect on the unitary smooth muscles and the other have a depolarizing effect on the unitary smooth muscles.

The compositions according to the invention can be packaged in different forms, for example in atomized form for use in a nasal spray or bronchial spray, in the form of an ampoule for nasal baths or sinus lavages by Proetz's method or for conversion to an aerosol, or alternatively in the form of a solution for use in a dropping bottle.

The pharmaceutical compositions according to the invention are generally administered 2 to 3 times a day, but this can vary according to the severity of the disease to be treated and the type of treatment, i.e. curative or preventive.

The following two compositions are now given as Examples which are particularly preferred for the purposes of the invention:

| Composition A | | Composition B | |
|---|---|---|---|
| (mg/l) | | (mg/l) | |
| ClNa | 8 | ClNa | 8 |
| ClK | 240 | ClK | 300 |
| Cl$_2$Mg(6H$_2$O) | 550 | Cl$_2$Mg(6H$_2$O) | 20 |
| Cl$_2$Ca(6H$_2$O) | 1 | Cl$_2$Ca(6H$_2$O) | 0.85 |
| Mannitol | 800 | Mannitol | 400 |
| D-Glucose | 7250 | D-Glucose | 6250 |
| L-Arginine hydrochloride | 2343 | L-Arginine hydrochloride | 2343 |
| Copper gluconate* | 7.25 | Zinc chloride** | 7.20 |
| Double-distilled water QSP | 1000 cc | Double-distilled water QSP | 1000 cc |

*corresponding amount of copper metal
**corresponding amount of zinc metal

ENT practice enables a daily check to be made on the efficacy of these compositions on numerous diseases of the upper respiratory tract.

Two distinctive physioanatomical properties of the nasal mucosae, one peculiar to the nasal cavities and the other characteristic of the respiratory mucosae, make it possible to visualize:

the depolarizing action of composition A on unitary smooth muscles deregulated by hyperpolarization, and the polarizing action of composition B on unitary smooth muscles deregulated by hyperdepolarization.

In fact, the presence of a vascular network with erectile tissue considerably amplifies any vasomotor manifestation, and the absence of loose tissue interposed between the respiratory mucosa and the underlying skeleton is such that all vasomotor manifestations are at the expense of the nasal lumen and obstruct the nasal cavity and meatus or, conversely, clear them.

Simple anterior rhinoscopy thus makes it possible to:

observe all volume and secretory modifications of the mucosa, all the more easily because these modifications take place in a few minutes or even, in some cases, in a few tenths of a second, and interpret the mechanisms involved, knowing that depolarization contracts the smooth muscle and empties the secretory cell of its secretions by contracting the myofibril, and that polarization has the opposite effects.

Two clinical forms of nasal obstruction, caused by vasomotor disorders of different etiopathogenesis, can serve as examples:

one form, of exogenous origin, is initiated by the dehydration of the mucosa: the heat then developed by friction between the airborne contaminants and the epithelium triggers an arteriovenous vasodilation by vagal reflex and a transitory seromucous hypersecretion by passive stretching of the myofibrils of the submucous glands. An examination performed a few hours later therefore shows the nasal cavities and meatus obstructed by a congestive mucosa often encrusted with dehydrated mucus.

the other example, of endogenous origin, can be initiated by the untimely intervention of various mediators with a depolarizing effect on the venular capillary sphincter. The tonic contraction of this sphincter causes a mechanical edema obstructing the nasal cavity and meatus, with pallor of the mucosa and cessation of the secretions.

Advantageously, compositions A and B will be administered sequentially, for example by spraying. Thus it is possible to administer composition A first, followed by composition B after about 1 to 2 minutes, or vice-versa.

For example, in the case of a nasal obstruction of exogenous origin, the spraying of composition A rapidly (in a few tenths of a second) causes retraction of the mucosa, clearing of the nasal cavity and meatus and a substantial seromucous secretion. By normalizing the seromucous secretion, the spraying of composition B 1 to 2 minutes later restores the glistening appearance of the mucosa and gives the feeling of drawing a "deeper and fresher" breath.

In the case of a nasal obstruction of endogenous origin, the spraying of composition B (about 1 to 2 minutes after that of composition A) clears the nasal cavity and meatus in 10 to 20 minutes and restores the normal volume and appearance (coloration and shine) of the mucosa. The relaxation of the venular sphincter effected by its polarization has lifted the capillary pressure generating the mechanical edema.

The presence of copper gluconate in composition A and Zn chloride in composition B has shown a synergistic action of these solutions in acute and especially subacute inflammatory states.

The proof of this synergistic action was provided by a study involving 2 series of 10 adult patients suffering from virosis of the upper respiratory tract with bilateral otitis and a negative tubal equipressure test.

Other inclusion criteria:

Subjective: More or less sharp bilateral otalgia. Bilateral hypacusis confirmed by the whispering test.

Objective: Congestive and retracted tympana with or without exudate from the cavity.

Exclusion criteria:

Unilateral or bilateral nasal obstruction coupled with substantial nasal septum deviation, or a polypoid degeneration of the mucosa or other underlying associated pathological condition.

Superacute otitis, phlyctenular otitis, suppurative otitis.

The experiment will consist in comparing the results obtained on homolateral otitis after spraying of the following:

In the 1st series: composition A+composition B into nasal cavity I and Cu+Zn into nasal cavity II.

In the 2nd series: composition A+composition B into nasal cavity I and $A_1+B_1$ into nasal cavity II ($A_1$ and $B_1$ correspond to compositions A and B without copper gluconate and, respectively, without zinc chloride).

Comments:

Nasal cavity I is the one corresponding to the car which appears to be clinically more affected.

A positive result is considered to be the clearing of the eustachian tube corresponding to the sprayed nasal cavity, effected within one hour, with a positive tubal equipressure test and the disappearance or improvement of the functional and objective signs.

Results:

|  | Nasal cavity I | Nasal cavity II | Positive results | |
|---|---|---|---|---|
|  |  |  | Nasal cavity I | Nasal cavity II |
| 1st series | A + B | Cu + Zn | 7 | 1 |
| 2nd series | A + B | $A_1 + B_1$ | 8 | 5 |
|  |  |  | 15 | 6 |

CONCLUSION: The overall action of the association of 2 principles:

on the one hand 2 solutions to be sprayed successively into the nasal cavities for the treatment of recurring diseases of the respiratory tract ($A_1+B_1$), and on the other hand a copper and zinc solution used in oligotherapy in infectious states (Cu+Zn), is superior to their 2 effects added together when the principles are separate, for the treatment of acute and especially subacute inflammatory states of the respiratory tract with sinusal or (and) auricular or (and) pharyngeal complications.

What is claimed is:

1. A pharmaceutical composition comprising an aqueous solution of:

a) a mixture of salts comprising a magnesium salt, sodium salt, a potassium salt and optionally, a calcium salt, said salts being present in a total amount of between 10 and 2000 mg/l;

b) at least one sugar, in an amount of between 200 and 10,000 mg/l;

c) at least one amino acid, in an amount of between 1 and 20 g/l; and d) a copper salt, wherein copper is present in an amount of between 5 and 100 mg/l, or a zinc salt, wherein zinc is present in an amount of between 5 and 120 mg/l.

2. The composition according to claim 1, wherein potassium and magnesium are present in a weight ratio K/Mg of between 0.40 and 0.85.

3. The composition according to claim 1, wherein potassium and magnesium are present in a weight ratio K/Mg of between 14 and 16.

4. The composition according to claim 3, wherein the salts are chlorides, and potassium and sodium are present in a weight ratio K/Na of between 30 and 40.

5. The composition according to claim 1, wherein the sugar is an absorbable sugar selected from the group consisting of glucose, galactose and xylose.

6. The composition according to claim 5, wherein the composition additionally comprises a non-absorbable sugar.

7. The composition according to claim 6, wherein the non-absorbable sugar is mannitol.

8. The composition according to claim 1, wherein the amino acid is selected from the group consisting of L-phenylalanine, L-arginine, and glutamic acid or a mixture thereof.

9. A kit comprising a plurality of pharmaceutical compositions, each of said pharmaceutical compositions comprising:
   a) a mixture of salts comprising a magnesium salt, a sodium salt, a potassium salt and optionally, a calcium salt, said salts being present in a total amount of between 10 and 2000 mg/l;
   b) at least one sugar, in an amount of between 200 and 10,000 mg/l;
   c) at least one amino acid, in an amount of between 1 and 20 q/l; and
   d) a copper salt, wherein copper is present in an amount of between 5 and 100 mg/l, or a zinc salt, wherein zinc is present in an amount of between 5 and 120 mg/l.

10. The kit according to claim 9, wherein the plurality comprises first and second pharmaceutical compositions.

11. The kit according to claim 10, wherein the first pharmaceutical composition comprises potassium and magnesium present in a weight ratio K/Mg of between 0.4 and 0.85, and the second pharmaceutical composition comprises potassium and magnesium present in a weight ratio K/Mg of between 14 and 16.

12. The kit according to claim 11, wherein the second pharmaceutical composition comprises potassium and sodium in a weight ratio K/Na of between 30 and 40.

13. The kit according to claim 10, wherein the first pharmaceutical composition comprises said copper salt, and the second composition comprises said zinc salt.

14. A pharmaceutical composition consisting essentially of an aqueous solution of:
   a) a mixture of a magnesium salt, a sodium salt and a potassium salt, and optionally, a calcium salt, said salts being present in a total amount of between 10 and 2000 mg/l;
   b) at least one sugar, in an amount of between 200 and 10,000 mg/l;
   c) at least one amino acid, in an amount of between 1 and 20 g/l; and
   d) a copper salt, wherein copper is present in an amount of between 5 and 100 mg/l, or a zinc salt, wherein zinc is present in an amount of between 5 and 120 mg/l.

* * * * *